US007893202B1

(12) United States Patent
Steward et al.

(10) Patent No.: US 7,893,202 B1
(45) Date of Patent: Feb. 22, 2011

(54) POST-TRANSLATIONAL MODIFICATIONS AND CLOSTRIDIAL NEUROTOXINS

(75) Inventors: Lance E. Steward, Irvine, CA (US); Ester Fernandez-Salas, Fullerton, CA (US); Athena Spanoyannis, Ashburn, VA (US); K. Roger Aoki, Coto de Caza, CA (US); Wei-Jen Lin, Cerritos, CA (US)

(73) Assignee: Allergan, Inc., Irvine, CA (US)

( * ) Notice: Subject to any disclaimer, the term of this patent is extended or adjusted under 35 U.S.C. 154(b) by 730 days.

(21) Appl. No.: 11/624,111

(22) Filed: Jan. 17, 2007

Related U.S. Application Data

(63) Continuation of application No. 11/141,513, filed on May 31, 2005, now Pat. No. 7,223,577, and a continuation-in-part of application No. 10/004,230, filed on Oct. 31, 2001, now abandoned.

(51) Int. Cl.
*A61K 39/00* (2006.01)
*C07K 1/00* (2006.01)

(52) U.S. Cl. .................................. 530/350; 424/185.1
(58) Field of Classification Search ....................... None
See application file for complete search history.

(56) References Cited

U.S. PATENT DOCUMENTS

| | | | |
|---|---|---|---|
| 5,837,265 | A | 11/1998 | Montal et al. |
| 5,989,545 | A | 11/1999 | Foster et al. |
| 6,573,071 | B1 * | 6/2003 | Himmelspach et al. .... 435/69.6 |
| 6,903,187 | B1 | 6/2005 | Steward et al. |
| 6,991,789 | B2 | 1/2006 | Li et al. |
| 7,223,577 | B2 | 5/2007 | Steward et al. |
| 7,393,925 | B2 | 7/2008 | Steward et al. |
| 7,491,799 | B2 | 2/2009 | Steward et al. |
| 7,534,863 | B2 | 5/2009 | Steward et al. |
| 7,556,817 | B2 | 7/2009 | Steward et al. |
| 2003/0027752 | A1 | 2/2003 | Steward et al. |
| 2003/0219462 | A1 | 11/2003 | Steward et al. |
| 2004/0219619 | A1 | 11/2004 | Fernandez-Salas et al. |
| 2004/0220386 | A1 | 11/2004 | Steward et al. |
| 2004/0228881 | A1 | 11/2004 | Steward et al. |
| 2006/0257430 | A1 | 11/2006 | Li et al. |
| 2008/0177037 | A1 | 7/2008 | Steward et al. |
| 2008/0177041 | A1 | 7/2008 | Steward et al. |
| 2008/0177042 | A1 | 7/2008 | Steward et al. |
| 2008/0194797 | A1 | 8/2008 | Steward et al. |
| 2008/0214781 | A1 | 9/2008 | Steward et al. |
| 2009/0118475 | A1 | 5/2009 | Steward et al. |

FOREIGN PATENT DOCUMENTS

| | | |
|---|---|---|
| WO | WO96/39166 | 12/1996 |
| WO | WO97/32599 | 9/1997 |
| WO | WO98/07864 | 2/1998 |
| WO | WO02/08268 | 1/2002 |

OTHER PUBLICATIONS

U.S. Appl. No. 10/004,230, filed Oct. 31, 2001, Steward et al.
U.S. Appl. No. 11/624,132, filed Jan. 17, 2007, Steward et al.
U.S. Appl. No. 11/624,146, filed Jan. 17, 2007, Steward et al.
U.S. Appl. No. 09/294,980, filed Apr. 19, 1999, Dolly et al.
U.S. Appl. No. 09/910,346, filed Jul. 20, 2001, Steward et al.
U.S. Appl. No. 11/620,579, filed Jan. 5, 2007, Steward et al.
U.S. Appl. No. 12/416,470, filed Apr. 1, 2009, Steward et al.
U.S. Appl. No. 12/434,074, filed May 1, 2009, Steward et al.
Encinar, J. A. et al., *Structural Stabilization of Botulinum Neurotoxins by Tyrosine Phosphorylation*, FEBS Lett. 429(1): 78-82 (1998).
Ferrer-Montiel, A. V. et al., *Tyrosine Phosphorylation Modulates the Activity of Clostridial Neurotoxins*, J. Biol. Chem. 271(31): 18322-18325 (1996).
Keller, J. E. et al., *Persistence of Botulinum Neurotoxin Action in Cultured Spinal Cord Cells*, FEBS Lett. 30;456(1): 137-142 (1999).
Kurazono, H. et al., *Minimal Essential Domains Specifying Toxicity of the Light Chains of Tetanus Toxin and Botulinum Neurotoxin Type A*, J. Biol. Chem. 267(21): 14721-14729 (1992).
Raciborska D. A. and Charlton, M. P., *Retention of Cleaved Synaptosome-Associated Protein of 25 Kda (SNAP-25) in Neuromuscular Junctions: A New Hypothesis to Explain Persistence of Botulinum A Poisoning* Can. J. Physiol. Pharmacol. 77(9):679-688 (1999).
Varshavsky, A., *The N-End Rule: Functions, Mysteries, Uses*, Proc Natl Acad Sci U S A. 93(22):12142-12149 (1996).
Aubert et al, "Circular Dichrosim Studies of Synthetic Asn-X-Ser/Thr-Containing Peptides: Structure-Glycosylation Relationship", Archives of Biochemistry and Biophysics, vol. 208, No. 1, pp. 20-29, 1981.
Gavel et al, "Sequence differences between glycosylated and non-glycosylated Asn-X-Thr/Ser acceptor sites: implications for protein engineering", Protein Engineering, vol. 3, No. 5, pp. 433-442, 1990.
Roitsch et al, Structural requirements for protein N-glycosylation, Eur. J. Biochem. 181, pp. 525-529, 1989.

* cited by examiner

*Primary Examiner*—Mark Navarro
(74) *Attorney, Agent, or Firm*—Kenton Abel; Dean Stathakis; Debra Condino

(57) ABSTRACT

The present invention discloses modified neurotoxins with altered biological persistence. In one embodiment, the modified neurotoxins are derived from *Clostridial botulinum* toxins. Such modified neurotoxins may be employed in treating various conditions, including but not limited to muscular disorders, hyperhidrosis, and pain.

13 Claims, No Drawings

```
                        SEQUENCE LISTING

<160> NUMBER OF SEQ ID NOS: 60

<210> SEQ ID NO 1
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 1

Asn Leu Thr Arg
 1

<210> SEQ ID NO 2
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 2

Asn Tyr Thr Ile
 1

<210> SEQ ID NO 3
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 3

Asn Phe Thr Lys
 1

<210> SEQ ID NO 4
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 4

Asn Phe Thr Gly
 1
```

```
<210> SEQ ID NO 5
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 5

Thr Asn Pro Glu
 1

<210> SEQ ID NO 6
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 6

Ser Tyr Tyr Asp
 1

<210> SEQ ID NO 7
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 7

Thr Asp Asn Glu
 1

<210> SEQ ID NO 8
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 8

Ser Thr Ile Asp
 1

<210> SEQ ID NO 9
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 9

Ser Gly Leu Glu
 1

<210> SEQ ID NO 10
<211> LENGTH: 4
<212> TYPE: PRT
```

```
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 10

Ser Phe Glu Glu
  1

<210> SEQ ID NO 11
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 11

Ser Leu Gln Glu
  1

<210> SEQ ID NO 12
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 12

Thr Ile Tyr Asp
  1

<210> SEQ ID NO 13
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: N-terminal myristylation site

<400> SEQUENCE: 13

Gly Val Asp Ile Ala Tyr
  1               5

<210> SEQ ID NO 14
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: N-terminal myristylation site

<400> SEQUENCE: 14

Gly Ser Tyr Arg Ser Glu
  1               5

<210> SEQ ID NO 15
<211> LENGTH: 6
<212> TYPE: PRT
<213> ORGANISM: Artificial Sequence
<220> FEATURE:
<221> NAME/KEY: SITE
<222> LOCATION: (1)...(6)
```

```
<223> OTHER INFORMATION: N-terminal myristylation site

<400> SEQUENCE: 15

Gly Leu Glu Val Ser Phe
 1               5

<210> SEQ ID NO 16
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 16

Ser Tyr Arg
 1

<210> SEQ ID NO 17
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 17

Ser Gly Lys
 1

<210> SEQ ID NO 18
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 18

Thr Ser Lys
 1

<210> SEQ ID NO 19
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tyrosine phosphorylation site

<400> SEQUENCE: 19

Lys Leu Phe Glu Arg Ile Tyr
 1               5

<210> SEQ ID NO 20
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: Tyrosine phosphorylation site

<400> SEQUENCE: 20
```

```
Lys Leu Lys Phe Asp Lys Leu Tyr
1               5

<210> SEQ ID NO 21
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 21

Asn Leu Ser Gly
1

<210> SEQ ID NO 22
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 22

Asn Gly Ser Gly
1

<210> SEQ ID NO 23
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 23

Asn Ser Ser Asn
1

<210> SEQ ID NO 24
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 24

Asn Ile Ser Leu
1

<210> SEQ ID NO 25
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 25

Asn Asp Ser Ile
1
```

```
<210> SEQ ID NO 26
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: N-glycosylation site

<400> SEQUENCE: 26

Asn Ile Ser Glu
  1

<210> SEQ ID NO 27
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 27

Thr Pro Gln Asp
  1

<210> SEQ ID NO 28
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 28

Ser Tyr Tyr Asp
  1

<210> SEQ ID NO 29
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 29

Ser Asp Glu Glu
  1

<210> SEQ ID NO 30
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 30

Ser Ala Val Glu
  1

<210> SEQ ID NO 31
<211> LENGTH: 4
<212> TYPE: PRT
<213> ORGANISM: Artificial Sequence
```

```
<220> FEATURE:
<221> NAME/KEY: SITE
<222> LOCATION: (1)...(4)
<223> OTHER INFORMATION: Casein kinase II phosphorylation site

<400> SEQUENCE: 31

Ser Met Asn Glu
 1

<210> SEQ ID NO 32
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 32

Thr Asn Ile Glu
 1

<210> SEQ ID NO 33
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 33

Ser Phe Thr Glu
 1

<210> SEQ ID NO 34
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Casein kinase II phosphorylation site

<400> SEQUENCE: 34

Thr Glu Phe Asp
 1

<210> SEQ ID NO 35
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: N-terminal myristylation site

<400> SEQUENCE: 35

Gly Leu Tyr Gly Ala Lys
 1               5

<210> SEQ ID NO 36
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: N-terminal myristylation site
```

```
<400> SEQUENCE: 36

Gly Thr Asp Leu Asn Ile
 1               5

<210> SEQ ID NO 37
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: N-terminal myristylation site

<400> SEQUENCE: 37

Gly Gln Asn Ala Asn Leu
 1               5

<210> SEQ ID NO 38
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 38

Ser Leu Lys
 1

<210> SEQ ID NO 39
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 39

Ser Leu Arg
 1

<210> SEQ ID NO 40
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 40

Ser Phe Arg
 1

<210> SEQ ID NO 41
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 41

Thr Thr Lys
```

```
<210> SEQ ID NO 42
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 42

Thr Gln Lys
1

<210> SEQ ID NO 43
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 43

Thr Gly Arg
1

<210> SEQ ID NO 44
<211> LENGTH: 3
<212> TYPE: PRT
<213> ORGANISM: Artificial Sequence
<220> FEATURE:
<221> NAME/KEY: SITE
<222> LOCATION: (1)...(3)
<223> OTHER INFORMATION: Protein kinase C phosphorylation site

<400> SEQUENCE: 44

Ser Val Lys
1

<210> SEQ ID NO 45
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tyrosine kinase phosphorylation site

<400> SEQUENCE: 45

Lys Asn Gly Asp Ser Ser Tyr
1               5

<210> SEQ ID NO 46
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: Tyrosine kinase phosphorylation site

<400> SEQUENCE: 46

Lys Asp Val Phe Glu Ala Lys Tyr
1               5

<210> SEQ ID NO 47
```

```
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/A light chain

<400> SEQUENCE: 47

Pro Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met
            20                  25

<210> SEQ ID NO 48
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/A light chain

<400> SEQUENCE: 48

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 49
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/B light chain

<400> SEQUENCE: 49

Pro Val Thr Ile Asn Asn Phe Asn Tyr Asn Asp Pro Ile Asp Asn Asp
1               5                   10                  15

Asn Ile Ile Met Met Glu Pro Pro Phe Ala Arg Gly Thr
            20                  25

<210> SEQ ID NO 50
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/B light chain

<400> SEQUENCE: 50

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His Leu Ala Val Tyr Lys Ile Gln Met Cys Lys Ser
        35                  40                  45
```

```
Val Lys
    50

<210> SEQ ID NO 51
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/C1 light chain

<400> SEQUENCE: 51

Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala
            20                  25

<210> SEQ ID NO 52
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/C1 light chain

<400> SEQUENCE: 52

Asn Ile Pro Lys Ser Asn Leu Asn Val Leu Phe Met Gly Gln Asn Leu
1               5                   10                  15

Ser Arg Asn Pro Ala Leu Arg Lys Val Asn Pro Glu Asn Met Leu Tyr
            20                  25                  30

Leu Phe Thr Lys Phe Cys His Lys Ala Ile Asp Gly Arg Ser Leu Tyr
        35                  40                  45

Asn Lys
    50

<210> SEQ ID NO 53
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/D light chain

<400> SEQUENCE: 53

Thr Trp Pro Val Lys Asp Phe Asn Tyr Ser Asp Pro Val Asn Asp Asn
1               5                   10                  15

Asp Ile Leu Tyr Leu Arg Ile Pro Gln Asn Lys Leu Ile
            20                  25

<210> SEQ ID NO 54
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/D light chain

<400> SEQUENCE: 54

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Leu Gln Lys Leu
```

```
                    20                  25                  30
Ser Ser Glu Ser Val Val Asp Leu Phe Thr Lys Val Cys Leu Arg Leu
        35                  40                  45

Thr Lys
    50

<210> SEQ ID NO 55
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/E light chain

<400> SEQUENCE: 55

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr
            20                  25

<210> SEQ ID NO 56
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/E light chain

<400> SEQUENCE: 56

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ile Ile Arg Phe Cys Lys Asn Ile Val Ser Val Lys Gly Ile
        35                  40                  45

Arg Lys
    50

<210> SEQ ID NO 57
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/F light chain

<400> SEQUENCE: 57

Pro Val Ala Ile Asn Ser Phe Asn Tyr Asn Asp Pro Val Asn Asp Asp
1               5                   10                  15

Thr Ile Leu Tyr Met Gln Ile Pro Tyr Glu Glu Lys Ser
            20                  25

<210> SEQ ID NO 58
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/F light chain

<400> SEQUENCE: 58
```

```
Thr Val Ser Glu Gly Phe Asn Ile Gly Asn Leu Ala Val Asn Arg
1               5                   10                  15

Gly Gln Ser Ile Lys Leu Asn Pro Lys Ile Ile Asp Ser Ile Pro Asp
            20                  25                  30

Lys Gly Leu Val Glu Lys Ile Val Lys Phe Cys Lys Ser Val Ile Pro
        35                  40                  45

Arg Lys
    50

<210> SEQ ID NO 59
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: N-terminal amino acids of BoNT/G light chain
<221> NAME/KEY: VARIANT
<222> LOCATION: 6
<223> OTHER INFORMATION: Xaa is any amino acid

<400> SEQUENCE: 59

Pro Val Asn Ile Lys Xaa Phe Asn Tyr Asn Asp Pro Ile Asn Asn Asp
1               5                   10                  15

Asp Ile Ile Met Met Glu Pro Phe Asn Asp Pro Gly Pro
            20                  25

<210> SEQ ID NO 60
<211> LENGTH: 50
<212> TYPE: PRT
<213> ORGANISM: Artificial Sequence
<220> FEATURE:
<221> NAME/KEY: DOMAIN
<222> LOCATION: (1)...(50)
<223> OTHER INFORMATION: C-terminal amino acids of BoNT/G light chain

<400> SEQUENCE: 60

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Tyr Glu Glu Ile Ser
            20                  25                  30

Leu Glu His Leu Val Ile Tyr Arg Ile Ala Met Cys Lys Pro Val Met
        35                  40                  45

Tyr Lys
    50
```

POST-TRANSLATIONAL MODIFICATIONS AND CLOSTRIDIAL NEUROTOXINS

This application is a continuation and claims priority pursuant to 35 U.S.C. §120 to U.S. patent application Ser. No. 11/141,513, filed May 31, 2005, now U.S. Pat. No. 7,223,577, a continuation in part application that claims priority pursuant to 35 U.S.C. §120 to U.S. patent application Ser. No. 10/004,230, filed Oct. 31, 2001, now abandoned, each which is hereby incorporated by reference in its entirety.

BACKGROUND

The present invention relates to modified neurotoxins, particularly modified *Clostridial* neurotoxins, and use thereof to treat various disorders, including neuromuscular disorders, autonomic nervous system disorders and pain.

The clinical use of botulinum toxin serotype A (herein after "BoNT/A"), a serotype of *Clostridial* neurotoxin, represents one of the most dramatic role reversals in modern medicine: a potent biologic toxin transformed into a therapeutic agent. BoNT/A has become a versatile tool in the treatment of a wide variety of disorders and conditions characterized by muscle hyperactivity, autonomic nervous system hyperactivity and/or pain.

One of the reasons that BoNT/A has been selected over the other serotypes, for example serotypes B, C.sub.1, D, E, F and G, for clinical use is that BoNT/A has a substantially longer lasting therapeutic effect. In other words, the inhibitory effect of BoNT/A is more persistent. Therefore, the other serotypes of botulinum toxins could potentially be effectively used in a clinical environment if their biological persistence could be enhanced. For example, parotoid sialocele is a condition where the patient suffers from excessive salivation. Sanders et al. disclose in their patent that serotype D may be very effective in reducing excessive salivation. However, the biological persistence of serotype D botulinum toxin is relatively short and thus may not be practical for clinical use. If the biological persistence of serotype D may be enhanced, it may effectively be used in a clinical environment to treat, for example, parotid sialocele.

Another reason that BoNT/A has been a preferred neurotoxin for clinical use is, as discussed above, its superb ability to immobilize muscles through flaccid paralysis. For example, BoNT/A is preferentially used to immobilize muscles and prevent limb movements after a tendon surgery to facilitate recovery. However, for some minor tendon surgeries, the healing time is relatively short. It would be beneficial to have a BoNT/A without the prolonged persistence for use in such circumstances so that the patient can regain mobility at about the same time the recover from the surgery.

Presently, the basis for the differences in persistence among the various botulinum toxins is unknown. However, there are two main theories explaining the differences in the persistence of the toxins. Without wishing to be bound by any theory of operation or mechanism of action, these theories will be discussed briefly below. The first theory proposes that the persistence of a toxin depends on which target protein and where on that target protein that toxin attacks. Raciborska et al., Can. J. Physiol. Pharmcol. 77:679-688 (1999). For example, SNAP-25 and VAMP are proteins required for vesicular docking, a necessary step for vesicular exocytosis. BoNT/A cleaves the target protein SNAP-25 and BoNT/B cleaves the target protein VAMP, respectively. The effect of each is similar in that cleavage of either protein compromises the ability of a neuron to release neurotransmitters via exocytosis. However, damaged VAMP may be more easily replaced with new ones that damaged SNAP-25, for example by replacement synthesis. Therefore, since it takes longer for cells to synthesize new SNAP-25 proteins to replace damaged ones, BoNT/A has longer persistence. Id. At 685.

Additionally, the site of cleavage by a toxin may dictate how quickly the damaged target proteins may be replaced. For example, BoNT/A and E both cleave SNAP-25. However, they cleave at different sites and BoNT/E causes shorter-lasting paralysis in patients, compared with BoNT/A. Id. At 685-6.

The second theory proposes that the particular persistence of a toxin depends on its particular intracellular half-life, or stability, i.e., the longer the toxin is available in the cell, the longer the effect. Keller et al., FEBS Letters 456:137-42 (1999). Many factors contribute to the intracellular stability of a toxin, but primarily, the better it is able to resist the metabolic actions of intracellular proteases to break it down, the more stable it is. Erdal et al. Naunyn-schmiedeber's Arch. Pharmacol. 351:67-78 (1995).

In general, the ability of a molecule to resist metabolic actions of intracellular proteases may depend on its structures. For example, the primary structure of a molecule may include a unique primary sequence which may cause the molecule to be easily degraded by proteases or difficult to be degraded. For example, Varshaysky A. describes polypeptides terminating with certain amino acids are more susceptible to degrading proteases. Proc. Natl. Acad. Sci. USA 93:12142-12149 (1996).

Furthermore, intracellular enzymes are known to modify molecules, for example polypeptides through, for example, N-glycosylation, phosphorylation etc. this kind of modification will be referred to herein as "secondary modification". "Secondary modification" often refers to the modification of endogenous molecules, for example, polypeptides after they are translated from RNAs. However, as used herein, "secondary modification" may also refer to an enzyme's, for example an intracellular enzyme's, ability to modify exogenous molecules. For example, after a patient is administered with exogenous molecules, e.g. drugs, these molecules may undergo a secondary modification by the action of the patient's enzymes, for example intracellular enzymes.

Certain secondary modifications of molecules, for example polypeptides, may resist or facilitate the actions of degrading proteases. These secondary modifications may, among other things, (1) affect the ability of a degrading protease to act directly on the molecule and/or (2) affect the ability of the molecules to be sequestered into vesicles to be protected against these degrading proteases.

There is a need to have modified neurotoxins which have efficacies of the various botulinum toxin serotypes, but with altered biological persistence, and methods for preparing such toxins.

SUMMARY OF THE INVENTION

The present invention meets this need and provides for modified neurotoxins with altered biological persistence and methods for preparing such toxins.

Without wishing to be limited by any theory or mechanism of operation, it is believed that Botulinum toxins have secondary modification sites, which may determine their biological persistence. A "secondary modification site" as used herein means a location on a molecule, for example a particular fragment or a polypeptide, which may be targeted by an enzyme, for example an intra-cellular enzyme, to affect a modification to the site, for example phosphorylation, glycosylation, etc. The secondary modification, for example phosphorylation, may help resist or facilitate the actions of degrading proteases acting on the toxins, which in turn increase or decrease the persistence, or stability, of the toxins, respectively. Alternatively, it is believed that these secondary modification sites may prevent or facilitate the transportation of the toxin into vesicles to be protected from degrading proteases. It is further believed that one of the roles of the secondary modification is to add to or take away the three dimensional and/or the chemical requirements necessary for protein interactions, for example between a molecule and a degrading protease, or a molecule and a vesicular transporter.

Therefore, a modified neurotoxin including a structural modification may have altered persistence as compared to an identical neurotoxin without the structural modification. The structural modification may include a partial or complete deletion or mutation of at least one modification site. Alternatively, the structural modification may include the addition of a certain modification site. In one embodiment, the altered persistence is the enhancement of the biological persistence. In another embodiment, the altered persistence is the reduction of biological persistence. Preferably, the altered persistence is affected by the alteration in the stability of the modified neurotoxin.

For example, the light chain of BoNT/A has amino acid fragments for various secondary modification sites (hereinafter "modification sites") including, but not limited to, N-glycosylation, casein kinase II (CK-2) phosphorylation, N-terminal myristylation, protein kinase C (PKC) phosphorylation and tyrosine phosphorylation. BoNT/E also has these various secondary modification sites. The structural modification includes the deletion or mutation of one or more of these secondary modification sites. The structural modification may also include the addition of one or more of a modification site to a neurotoxin to form a modified neurotoxin. This invention also provide for methods of producing modified neurotoxins. Additionally, this invention provide for methods of using the modified neurotoxins to treat biological disorders.

DEFINITIONS

Before proceeding to describe the present invention, the following definitions are provided and apply herein.

"Heavy chain" means the heavy chain of a *Clostridial* neurotoxin. It preferably has a molecular weight of about 100 kD and may be referred to herein as H chain or as H.

"$H_N$" means a fragment (preferably having a molecular weight of about 50 kD) derived from the H chain of a *Clostridial* neurotoxin which is approximately equivalent to the amino terminal segment of the H chain, or the portion corresponding to that fragment in the intact in the H chain. It is believed to contain the portion of the natural or wild type *Clostridial* neurotoxin involved in the translocation of the L chain across an intracellular endosomal membrane.

"$H_C$" means a fragment (about 50 kD) derived from the H chain of a *Clostridial* neurotoxin which is approximately equivalent to the carboxyl terminal segment of the H chain, or the portion corresponding to that fragment in the intact H chain. It is believed to be immunogenic and to contain the portion of the natural or wild type *Clostridial* neurotoxin involved in high affinity, presynaptic binding to motor neurons.

"Light chain" means the light chain of a *Clostridial* neurotoxin. It preferably has a molecular weight of about 50 kD, and can be referred to as L chain, L or as the proteolytic domain (amino acid sequence) of a *Clostridial* neurotoxin. The light chain is believed to be effective as an inhibitor of neurotransmitter release when it is released into a cytoplasm of a target cell.

"Neurotoxin" means a molecule that is capable of interfering with the functions of a neuron. The "neurotoxin" may be naturally occurring or man-made.

"Modified neurotoxin" means a neurotoxin which includes a structural modification. In other words, a "modified neurotoxin" is a neurotoxin which has been modified by a structural modification. The structural modification changes the biological persistence, preferably the biological half-life, of the modified neurotoxin relative to the neurotoxin from which the modified neurotoxin is made. The modified neurotoxin is structurally different from a naturally existing neurotoxin.

"Structural modification" means a physical change to the neurotoxin that may be affected by, for example, covalently fusing one or more amino acids to the neurotoxin. "Structural modification" also means the deletion of one or more amino acids from a neurotoxin. Furthermore, "structural modification" may also mean any changes to a neurotoxin that makes it physically or chemically different from an identical neurotoxin without the structural modification.

"Biological persistence" means the time duration in which a neurotoxin or a modified neurotoxin causes an interference with a neuronal function, for example the time duration in which a neurotoxin or a modified neurotoxin causes a substantial inhibition of the release of acetylcholine from a nerve terminal.

"Biological half-life" means the time that the concentration of a neurotoxin or a modified neurotoxin, preferably the active portion of the neurotoxin or modified neurotoxin, for example the light chain of botulinum toxins, is reduced to half of the original concentration in a mammal, preferably in the neurons of the mammal.

"Modification site" means a particular amino acid or a fragment of amino acids where upon secondary modification may takes place. "Modification site" may also mean a particular amino acid or a particular fragment of amino acids necessary for a certain secondary modification to occur.

DETAILED DESCRIPTION OF THE INVENTION

The present invention is, in part, based upon the discovery that the biological persistence of a neurotoxin may be altered by structurally modifying the neurotoxin. In other words, a modified neurotoxin with an altered biological persistence may be formed from a neurotoxin containing or including a structural modification. Preferably, the inclusion of the structural modification may alter the biological half-life of the modified neurotoxin. An altered biological persistence, preferably an altered biological half-life, means that the biological persistence (or biological half-life) of a modified neurotoxin is different from that of an identical neurotoxin without the structural modification. Additionally, the biological persistence, preferably the biological half-life, may be altered to be longer or shorter.

In one embodiment, the structural modification includes a partial or complete deletion or mutation of the modification site of the neurotoxin to form a modified neurotoxin. The inclusion of the modification site may enhance the biological persistence of the modified neurotoxin. Preferably, the partial or complete deletion, or mutation of the modification site enhances the biological half-life of the modified neurotoxin. More preferably, the biological half-life of the modified neurotoxin is enhanced by about 10%. Even more preferably, the biological half-life of the modified neurotoxin is enhanced by about 100%. Generally speaking, the modified neurotoxin has a biological persistence of about 20% to 300% more than an identical neurotoxin without the structural modification. That is, for example, the modified neurotoxin including the modified modification site is able to cause a substantial inhibition of acetylcholine release from a nerve terminal for about 20% to about 300% longer than a neurotoxin that is not modified.

In one embodiment, the structural modification includes a partial or complete deletion or mutation of the modification site of the neurotoxin to form a modified neurotoxin. The inclusion of the modification site may reduce the biological persistence of the modified neurotoxin. Preferably, the partial or complete deletion, or mutation of the modification site reduces the biological half-life of the modified neurotoxin. More preferably, the biological half-life of the modified neurotoxin is reduced by about 10%. Even more preferably, the biological half-life of the modified neurotoxin is reduced by about 99%. Generally speaking, the modified neurotoxin has a biological persistence of about 20% to 300% less than an identical neurotoxin without the structural modification. That is, for example, the modified neurotoxin including the modified modification site is able to cause a substantial inhibition of acetylcholine release from a nerve terminal for about 20% to about 300% shorter in time than a neurotoxin that is not modified.

For example, BoNT/A and BoNT/E have the following potential secondary modification sites as shown on Tables 1 and 2, respectively.

TABLE 1

| N-glycosylation sites |
|---|
| 173-NLTR (SEQ ID NO: 1) |
| 382-NYTI (SEQ ID NO: 2) |
| 411-NFTK (SEQ ID NO: 3) |
| 417-NFTG (SEQ ID NO: 4) |
| Casein kinase II (CK-2) phosphorylation sites |
| 51-TNPE (SEQ ID NO: 5) |
| 70-SYYD (SEQ ID NO: 6) |
| 79-TDNE (SEQ ID NO: 7) |
| 120-STID (SEQ ID NO: 8) |
| 253-SGLE (SEQ ID NO: 9) |
| 258-SFEE (SEQ ID NO: 10) |
| 275-SLQE (SEQ ID NO: 11) |
| 384-TIYD (SEQ ID NO: 12) |
| N-terminal myristylation sites |
| 15-GVDIAY (SEQ ID NO: 13) |
| 141-GSYRSE (SEQ ID NO: 14) |
| 254-GLEVSF (SEQ ID NO: 15) |
| Protein kinase C (PKC) phosphorylation sites |
| 142-SYR (SEQ ID NO: 16) |
| 327-SGK (SEQ ID NO: 17) |
| 435-TSK (SEQ ID NO: 18) |

TABLE 1-continued

| Tyrosine phosphorylation sites |
|---|
| 92-KLFERIY (SEQ ID NO: 19) |
| 334-KLKFDKLY (SEQ ID NO: 20) |

TABLE 2

| N-glycosylation sites |
|---|
| 97-NLSG (SEQ ID NO: 21) |
| 138-NGSG (SEQ ID NO: 22) |
| 161-NSSN (SEQ ID NO: 23) |
| 164-NISL (SEQ ID NO: 24) |
| 365-NDSI (SEQ ID NO: 25) |
| 370-NISE (SEQ ID NO: 26) |
| Casein kinase II (CK-2) phosphorylation sites |
| 51-TPQD (SEQ ID NO: 27) |
| 67-SYYD (SEQ ID NO: 28) |
| 76-SDEE (SEQ ID NO: 29) |
| 130-SAVE (SEQ ID NO: 30) |
| 198-SMNE (SEQ ID NO: 31) |
| 247-TNIE (SEQ ID NO: 32) |
| 333-SFTE (SEQ ID NO: 33) |
| 335-TEFD (SEQ ID NO: 34) |
| N-terminal myristylation sites |
| 220-GLYGAK (SEQ ID NO: 35) |
| 257-GTDLNI (SEQ ID NO: 36) |
| 386-GQNANL (SEQ ID NO: 37) |
| Protein kinase C (PKC) phosphorylation sites |
| 60-SLK (SEQ ID NO: 38) |
| 166-SLR (SEQ ID NO: 39) |
| 191-SFR (SEQ ID NO: 40) |
| 228-TTK (SEQ ID NO: 41) |
| 234-TQK (SEQ ID NO: 42) |
| 400-TGR (SEQ ID NO: 43) |
| 417-SVK (SEQ ID NO: 44) |
| Tyrosine kinase phosphorylation sites |
| 62-KNGDSSY (SEQ ID NO: 45) |
| 300-KDVFEAKY (SEQ ID NO: 46) |

In one preferred embodiment, one or more of the modification site of BoNT/A, for example the N-glycosylation site, is partially deleted, completely deleted or mutated, resulting in a modified neurotoxin with an altered biological persistence, preferably an altered biological half-life. In one embodiment, the modified neurotoxin is altered to have a longer biological persistence, preferably longer biological half-life. In another embodiment, the modified neurotoxin is altered to have a shorter persistence, preferably a shorter biological half-life.

In one preferred embodiment, one or more of the modification site of BoNT/E, for example the N-glycosylation site, is partially deleted, completely deleted or mutated, resulting in a modified neurotoxin with an altered biological persistence, preferably an altered biological half-life. In one embodiment, the modified neurotoxin is altered to have a longer biological persistence, preferably longer biological half-life. In another embodiment, the modified neurotoxin is altered to have a shorter persistence, preferably a shorter biological half-life as compared to an identical neurotoxin without the structural modification.

In one broad embodiment, the modified neurotoxin may include additional modification sites fused onto neurotoxins to form modified neurotoxins. The modification sites may be any modification sites known in the art, including the ones listed on Tables 1 and 2. In one embodiment, such inclusion of the modification site may enhance the biological persistence of the modified neurotoxin. Preferably, the modification site enhances the biological half-life of the modified neurotoxin. More preferably, the biological half-life of the modified neurotoxin is enhanced by about 10%. Even more preferably, the biological half-life of the modified neurotoxin is enhanced by about 100%. Generally speaking, the modified neurotoxin has a biological persistence of about 20% to 300% more than an identical neurotoxin without the structural modification. That is, for example, the modified neurotoxin including the modified site is able to cause a substantial inhibition of acetylcholine release from a nerve terminal for about 20% to about 300% longer than a neurotoxin that is not modified. A non-limiting example of a modified neurotoxin with an additional modification site is Bo/E with a casein kinase II phosphorylation site, preferably TDNE, fused to its primary structure. More preferably, the TDNE is fused to position 79 of BoNT/E or a position on BoNT/E which substantially corresponds to position 79 of BoNT/A.

In one broad embodiment, the modified neurotoxin may include additional modification sites fused onto neurotoxins to form modified neurotoxins. The modification sites may be any modification sites known in the art, including the ones listed on Tables 1 and 2. In one embodiment, such inclusion of the modification site may reduce the biological persistence of the modified neurotoxin. Preferably, the modification site reduces the biological half-life of the modified neurotoxin. More preferably, the biological half-life of the modified neurotoxin is reduced by about 10%. Even more preferably, the biological half-life of the modified neurotoxin is reduced by about 99%. Generally speaking, the modified neurotoxin has a biological persistence of about 20% to 300% less than an identical neurotoxin without the structural modification. That is, for example, the modified neurotoxin including the modified site is able to cause a substantial inhibition of acetylcholine release from a nerve terminal for about 20% to about 300% shorter in time than a neurotoxin that is not modified. A non-limiting example of a modified neurotoxin with an additional modification site is Bo/A with a casein kinase II phosphorylation site, preferably SDEE, fused to its primary structure. More preferably, the SDEE is fused to position 76 of BoNT/A or a position on BoNT/A which substantially corresponds to position 76 of BoNT/E.

In one embodiment, the structural modification may include the addition and the partial or complete deletion or mutation of modification sites. For example, a modified neurotoxin may be BoNT/A with GVDIAY at position 15 deleted and includes a SLK fragment for protein kinase C phosphorylation. The SLK fragment is preferably fused to position 60 of BoNT/A or a position on BoNT/A which substantially corresponds to position 60 of BoNT/E. The modified neurotoxin according to this embodiment may have altered biological persistence. In one embodiment, the biological persistence is increased. In another embodiment, the biological persistence is decreased. Preferably, the modified neurotoxin according to this embodiment may have altered biological half-life. In one embodiment, the biological half-life is increased. In another embodiment, the biological half-life is decreased.

In one broad aspect of the present invention, a method is provided for treating a biological disorder using a modified neurotoxin. The treatments may include treating neuromuscular disorders, autonomic nervous system disorders and pain.

The neuromuscular disorders and conditions that may be treated with a modified neurotoxin include: for example, strabismus, blepharospasm, spasmodic torticollis (cervical dystonia), oromandibular dystonia and spasmodic dysphonia (laryngeal dystonia).

For example, Borodic U.S. Pat. No. 5,053,005 discloses methods for treating juvenile spinal curvature, i.e. scoliosis, using BoNT/A. The disclosure of Borodic is incorporated in its entirety herein by reference. In one embodiment, using substantially similar methods as disclosed by Borodic, a modified neurotoxin is administered to a mammal, preferably a human, to treat spinal curvature. In a preferred embodiment, a modified neurotoxin comprising BoNT/E fused with an N-terminal myristylation site is administered. Even more preferably, a modified neurotoxin comprising BoNT/E with an N-terminal myristylation site fused to position 15 of its light chain, or a position substantially corresponding to position 15 of the BoNT/A light chain, is administered to the mammal, preferably a human, to treat spinal curvature. The modified neurotoxin may be administered to treat other neuromuscular disorders using well known techniques that are commonly performed with BoNT/A.

Autonomic nervous system disorders may also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. discloses methods for treating the autonomic nervous system, such as excessive sweating, excessive salivation, asthma, etc., using naturally existing botulinum toxins. The disclosure of Sander et al. is incorporated in its entirety by reference herein. In one embodiment, substantially similar methods to that of Sanders et al. may be employed, but using a modified neurotoxin, to treat autonomic nervous system disorders such as the ones discussed above. For example, a modified neurotoxin may be locally applied to the nasal cavity of the mammal in an amount sufficient to degenerate cholinergic neurons of the autonomic nervous system that control the mucous secretion in the nasal cavity.

Pain that may be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy may be treated with a naturally occurring botulinum toxin, for example BoNT/A. The disclosure of Binder is incorporated in its entirety herein by reference. In one embodiment, substantially similar methods to that of Binder may be employed, but using a modified neurotoxin, to treat headache, especially the ones caused by vascular disturbances, muscular tension, neuralgia and neuropathy. Pain caused by muscle spasm may also be treated by an administration of a modified neurotoxin. For example, a modified neurotoxin comprising BoNT/E with an N-terminal myristylation site fused to position 15 of its light chain, or a position substantially corresponding to position 15 of the BoNT/A light chain, may be administered intramuscularly at the pain/spasm location to alleviate pain.

Furthermore, a modified neurotoxin may be administered to a mammal to treat pain that is not associated with a muscular disorder, such as spasm. In one broad embodiment, methods of the present invention to treat non-spasm related pain include central administration or peripheral administration of the modified neurotoxin.

For example, Foster et al. in U.S. Pat. No. 5,989,545 discloses that a botulinum toxin conjugated with a targeting moiety may be administered centrally (intrathecally) to alleviate pain. The disclosure of Foster et al. is incorporated in its entirety by reference herein. In one embodiment, substantially similar methods to that of Foster et al. may be employed, but using the modified neurotoxin according to this invention, to treat pain. The pain to be treated may be an acute pain, or preferably, chronic pain.

An acute or chronic pain that is not associated with a muscle spasm may also be alleviated with a local, peripheral administration of the modified neurotoxin to an actual or a perceived pain location on the mammal. In one embodiment, the modified neurotoxin is administered subcutaneously at or near the location of pain, for example at or near a cut. In another embodiment, the modified neurotoxin is administered intramuscularly at or near the location of pain, for example at or near a bruise location on the mammal. In another embodiment, the modified neurotoxin is injected directly into a joint of a mammal, for treating or alleviating pain cause arthritis conditions. Also, frequent repeated injections or infusion of the modified neurotoxin to a peripheral pain location is within the scope of the present invention. However, given the long lasting therapeutic effects of the present invention, frequent injections or infusion of the neurotoxin may not be necessary. For example, practice of the present invention can provide an analgesic effect, per injection, for 2 months or longer, for example 27 months, in humans.

Without wishing to limit the invention to any mechanism or theory of operation, it is believed that when the modified neurotoxin is administered locally to a peripheral location, it inhibits the release of neuro-substances, for example substance P, from the peripheral primary sensory terminal. Since the release of substance P by the peripheral primary sensory terminal may cause or at least amplify pain transmission process, inhibition of its release at the peripheral primary sensory terminal will dampen the transmission of pain signals from reaching the brain.

In addition to having pharmacologic actions at the peripheral location, the modified neurotoxin of the present invention may also have inhibitory effects in the central nervous system. Presumably the retrograde transport is via the primary afferent. This hypothesis is supported by our experimental data which shows that BoNT/A is retrograde transported to the dorsal horn when the neurotoxin is injected peripherally. Moreover, work by Weigand et al, Nauny-Schmiedeberg's Arch. Pharmacol. 1976; 292, 161-165, and Habermann, Nauny-Schmiedeberg's Arch. Pharmacol. 1974; 281, 47-56, showed that botulinum toxin is able to ascend to the spinal area by retrograde transport. As such, a modified neurotoxin, for example BoNT/A with one or more amino acids deleted from the leucine-based motif, injected at a peripheral location, for example intramuscularly, may be retrograde transported from the peripheral primary sensory terminal to the central primary sensory terminal.

The amount of the modified neurotoxin administered can vary widely according to the particular disorder being treated, its severity and other various patient variables including size, weight, age, and responsiveness to therapy. Generally, the dose of modified neurotoxin to be administered will vary with the age, presenting condition and weight of the mammal, preferably a human, to be treated. The potency of the modified neurotoxin will also be considered.

Assuming a potency which is substantially equivalent to $LD_{50}=2,730$ U in a human patient and an average person is 75 kg, a lethal dose would be about 36 U/kg of a modified neurotoxin. Therefore, when a modified neurotoxin with such an $LD_{50}$ is administered, it would be appropriate to administer less than 36 U/kg of the modified neurotoxin into human subjects. Preferably, about 0.01 U/kg to 30 U/kg of the modified neurotoxin is administered. More preferably, about 1 U/kg to about 15 U/kg of the modified neurotoxin is administered. Even more preferably, about 5 U/kg to about 10 U/kg modified neurotoxin is administered. Generally, the modified neurotoxin will be administered as a composition at a dosage that is proportionally equivalent to about 2.5 cc/100 U. Those of ordinary skill in the art will know, or can readily ascertain, how to adjust these dosages for neurotoxin of greater or lesser potency.

Although examples of routes of administration and dosages are provided, the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14.sup.th edition, published by McGraw Hill). For example, the route and dosage for administration of a modified neurotoxin according to the present disclosed invention can be selected based upon criteria such as the solubility characteristics of the modified neurotoxin chosen as well as the types of disorder being treated.

The modified neurotoxin may be produced by chemically linking the modification sites to a neurotoxin using conventional chemical methods well known in the art. The neurotoxin may be obtained from harvesting neurotoxins. For example, BoNT/E can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNT/B serotype only cleave a portion of the toxin produced. The exact proportion of nicked to unnicked molecules depends on the length of incubation and the temperature of the culture. Therefore, a certain percentage of any preparation of, for example, the BoNT/B toxin is likely to be inactive, possibly accounting for the known significantly lower potency of BoNT/B as compared to BoNT/A. The presence of inactive botulinum toxin molecules in a clinical preparation will contribute to the overall protein load of the preparation, which has been linked to increased antigenicity, without contributing to its clinical efficacy. Additionally, it is known that BoNT/B has, upon intramuscular injection, a shorter duration of activity and is also less potent than BoNT/A at the same dose level.

The modified neurotoxin may also be produced by recombinant techniques. Recombinant techniques are preferable for producing a neurotoxin having amino acid sequence regions from different *Clostridial* species or having modified amino acid sequence regions. Also, the recombinant technique is preferable in producing BoNT/A with the modified (deleted or mutated) or added modification sites. The technique includes steps of obtaining genetic materials from natural sources, or synthetic sources, which have codes for a neuronal binding moiety, an amino acid sequence effective to translocate the neurotoxin or a part thereof, and an amino acid sequence having therapeutic activity when released into a cytoplasm of a target cell, preferably a neuron. In a preferred embodiment, the genetic materials have codes for the biological persistence enhancing component, preferably the leucine-based motif, the H.sub.C, the H.sub.N and the L chain of the *Clostridial* neurotoxins and fragments thereof. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques.

There are many advantages to producing these modified neurotoxins recombinantly. For example, to form a modified neurotoxin, a modifying fragment must be attached or inserted into a neurotoxin. The production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous *Clostridial* proteases through a process termed nicking to create a dichain. Sometimes, the process of nicking involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the serotype and amounts of proteolytic activity produced by a given strain. For example, greater than 99% of *Clostridial* botulinum serotype A single-chain neurotoxin is activated by the Hall A *Clostridial* botulinum strain, whereas serotype B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered *Clostridial* toxins is, therefore, an important consideration for manufacture of these materials. It would be a major advantage if neurotoxins such as botulinum toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and botulinum toxins; these isolated chains are, by themselves, non-toxic; see Li et al., Biochemistry 33:7014-7020 (1994); Zhou et al., Biochemistry 34:15175-15181 (1995), hereby incorporated by reference herein. Following the separate production of these peptide chains and under strictly controlled conditions the H and L chains can be combined by oxidative disulphide linkage to form the neuroparalytic di-chains(di-polypeptide), linked together by a disulfide bond. Preferably one of the polypeptides is a *Clostridial* neurotoxin heavy chain and the other is a *Clostridial* neurotoxin light chain. The neuronal binding moiety is preferably part of the heavy chain.

EXAMPLES

The following non-limiting examples provide those of ordinary skill in the art with specific preferred methods to treat non-spasm related pain within the scope of the present invention and are not intended to limit the scope of the invention.

Example 1

Treatment of Pain Associated with Muscle Disorder

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is injected with about 8 U/kg to about 15 U/kg of the modified neurotoxin into the masseter and temporalis muscles, preferably the modified neurotoxin comprises BoNT/E with an N-terminal myristylation site, for example GVDIAY, fused to position 15 of its light chain, or a position substantially corresponding to position 15 of the BoNT/A light chain.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 2

Treatment of Pain Subsequent to Spinal Cord Injury

A patient, age 39, experiencing pain subsequent to spinal cord injury is treated by intrathecal administration, for example by spinal tap or by catherization (for infusion), to the spinal cord, with about 0.1 U/kg to about 10 U/kg of the modified neurotoxin, preferably the modified neurotoxin comprises BoNT/E with an N-terminal myristylation site, for example GVDIAY, fused to position 15 of its light chain, or a position substantially corresponding to position 15 of the BoNT/A light chain. The particular toxin dose and site of injection, as well as the frequency of toxin administrations depend upon a variety of factors within the skill of the treating physician, as previously set forth. Within about 1 to about 7 days after the modified neurotoxin administration, the patient's pain is substantially reduced. The pain alleviation persists for up to 27 months.

Example 3

Peripheral Administration of a Modified Neurotoxin to Treat "Shoulder-Hand Syndrome"

Pain in the shoulder, arm, and hand can develop, with muscular dystrophy, osteoporosis, and fixation of joints. While most common after coronary insufficiency, this syndrome may occur with cervical osteoarthritis or localized shoulder disease, or after any prolonged illness that requires the patient to remain in bed.

A 46 year old woman presents a shoulder-hand syndrome type pain. The pain is particularly localized at the deltoid region. The patient is treated by a bolus injection of about 0.05 U/kg to about 2 U/kg of a modified neurotoxin subcutaneously to the shoulder, preferably the modified neurotoxin comprises BoNT/E with an N-terminal myristylation site, for example GVDIAY, fused to position 15 of its light chain, or a position substantially corresponding to position 15 of the BoNT/A light chain. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 4

Peripheral Administration of a Modified Neurotoxin to Treat Postherpetic Neuralgia Postherpetic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherpetic neuralgia may occur anywhere, but is most often in the thorax.

A 76 year old man presents a postherpetic type pain. The pain is localized to the abdomen region. The patient is treated by a bolus injection of between about 0.05 U/kg to about 2 U/kg of a modified neurotoxin intradermally to the abdomen, preferably the modified neurotoxin comprises BoNT/E with an N-terminal myristylation site, for example GVDIAY, fused to position 15 of its light chain, or a position substantially corresponding to position 15 of the BoNT/A light chain. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 5

Peripheral Administration of a Modified Neurotoxin to Treat Nasopharyngeal Tumor Pain These tumors, most often squamous cell carcinomas, are usually in the fossa of Rosenmuller and may invade the base of the skull. Pain in the face is common. It is constant, dull-aching in nature.

A 35 year old man presents a nasopharyngeal tumor type pain. Pain is found at the lower left cheek. The patient is treated by a bolus injection of between about 0.05 U/kg to about 2 U/kg of a modified neurotoxin intramuscularly to the cheek, preferably the modified neurotoxin comprises BoNT/E with an N-terminal myristylation site, for example GVDIAY, fused to position 15 of its light chain, or a position substantially corresponding to position 15 of the BoNT/A light chain. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 6

Peripheral Administration of a Modified Neurotoxin to Treat Inflammatory Pain

A patient, age 45, presents an inflammatory pain in the chest region. The patient is treated by a bolus injection of between about 0.05 U/kg to about 2 U/kg of a modified neurotoxin intramuscularly to the chest, preferably the modified neurotoxin comprises BoNT/E with an N-terminal myristylation site, for example GVDIAY, fused to position 15 of its light chain, or a position substantially corresponding to position 15 of the BoNT/A light chain. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 7

Treatment of Excessive Sweating

A male, age 65, with excessive unilateral sweating is treated by administering 0.05 U/kg to about 2 U/kg of a modified neurotoxin, depending upon degree of desired effect. Preferably the modified neurotoxin comprises BoNT/E with an N-terminal myristylation site, for example GVDIAY, fused to position 15 of its light chain, or a position substantially corresponding to position 15 of the BoNT/A light chain. The administration is to the gland nerve plexus,

Example 8

Post Surgical Treatments

A female, age 22, presents a torn shoulder tendon and undergoes orthopedic surgery to repair the tendon. After the surgery, the patient is administered intramuscularly with about 0.05 U/kg to about 2 U/kg of a modified neurotoxin to the shoulder. Preferably, the modified neurotoxin comprises BoNT/A with an N-terminal myristylation site, for example GLEVSF at position 254, deleted. The specific site of administration is to be determined by the physician's knowledge of the anatomy and physiology of the muscles. The administered modified neurotoxin reduces movement of the arm to facilitate the recovery from the surgery. The effect of the modified neurotoxin is for about five weeks.

Example 9

Treatment of Spasmodic Dysphonia

A male, age 45, unable to speak clearly, due to spasm of the vocal chords, is treated by injection of the vocal chords with a bout 0.1 U/kg to about 2 U/kg of modified neurotoxins according to the present invention. After 3-7 days, the patient is able to speak clearly. The patient's condition is alleviated for about 7 months to about 27 months.

Example 10

Treatment of Spasmodic Torticollis

A male, age 45, suffering from spasmodic torticollis, as manifested by spasmodic or tonic contractions of the neck musculature, producing stereotyped abnormal deviations of the head, the chin being rotated to the side, and the shoulder being elevated toward the side at which the head is rotated, is treated by injection with about 8 U/kg to about 15 U/kg of neurotoxins according to the present invention. After 3-7 days, the symptoms are substantially alleviated; i.e., the patient is able to hold his head and shoulder in a normal position. The alleviation persists for about 7 months to about 27 months.

Example 11

Treatment of Essential Tremor

A male, age 45, suffering from essential tremor, which is manifested as a rhythmical oscillation of head or hand muscles and is provoked by maintenance of posture or movement, is treated by injection with about 8 U/kg to about 15 U/kg of modified neurotoxin of the present invention. After two to eight weeks, the symptoms are substantially alleviated; i.e., the patient's head or hand ceases to oscillate. The symptoms are alleviated for about 5 months to about 27 months.

ganglion, spinal cord or central nervous system. The specific site of administration is to be determined by the physician's knowledge of the anatomy and physiology of the target glands and secretary cells. In addition, the appropriate spinal cord level or brain area can be injected with the toxin. The cessation of excessive sweating after the modified neurotoxin treatment is up to 27 months.

Example 12

Production of a Modified Neurotoxin with an Altered Biological Persistence

A modified neurotoxin according to the present invention may be produced with recombinant techniques. An example of a recombinant technique is one which includes the step of obtaining genetic materials from oligonucleotide sequences having codes for a modified neurotoxin according to the present invention. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques. See also International Patent Application WO95/32738, the disclosure of which is incorporated in its entirety by reference herein. The modified neurotoxin produced according to this example has an altered biological persistence. Preferably, the biological persistence is enhanced, more preferably enhanced by about 20% to about 300% relative to an identical neurotoxin without a leucine-based motif.

Example 13

Modified Botulinum Toxins Having Additional Tyrosine Phosphorylation Sites

In some embodiments, modified botulinum toxins of this invention comprise one or more tyrosine phosphorylation sites in addition to any naturally existing ones. In some embodiments, the modified botulinum toxins comprise a heavy chain (modified or unmodified) and a modified botulinum toxin light chain, wherein the modified light chain comprises one or more tyrosine phosphorylation sites in addition to any naturally existing ones. For example, the amino acid sequence of a modified toxin, or the light chain thereof, of the present invention is identical to that of a naturally existing toxin, except for the added tyrosine phosphorylation site(s).

Without wishing to limit the invention to any theory or mechanism of operation, it is believed that the additional tyrosine phosphorylation site increases the biological persistence of the modified botulinum toxin. Any tyrosine phosphorylation site may be employed in accordance with the present invention. Non-limiting examples of tyrosine phosphorylation sites include KLFERIY, KLKFDKLY, and the tyrosine-based motif.

In some embodiments, a tyrosine-based motif may comprise four amino acids. The amino acid at the N-terminal end of the tyrosine-based motif can be a tyrosine. The amino acid at the C-terminal end of the tyrosine-based motif can be a hydrophobic amino acid. The two amino acids between the N-terminus and the C-terminus may be any amino acid. In some embodiments, the tyrosine-based motif comprises the sequence YKLL.

In some embodiments, a modified botulinum toxin of the present invention comprises at least one tyrosine phosphorylation site, e.g., a tyrosine-based motif, at the N-terminal of the light chain. In some embodiments, a modified botulinum toxin of the present invention comprises at least one tyrosine phosphorylation site, e.g., a tyrosine-based motif, at the C-terminal of the light chain. In some embodiments, a modified botulinum toxin of the present invention comprises a tyrosine phosphorylation site, e.g., tyrosine-based motif, at the N-terminal and C-terminal of the light chain.

Table 3 below shows the N-terminal and C-terminal regions of the light chain of botulinum toxin types A-G. A modified botulinum toxin of the present invention may comprise a tyrosine phosphorylation site, e.g., a tyrosine-based motif, added to or substituted into the N-terminal and/or C-terminal region of the light chains of the respective botulinum toxins. In some embodiments, a tyrosine phosphorylation site may substitute 1-10 consecutive amino acids of the light chain. In some embodiments, the tyrosine phosphorylation site may substitute about 1-8, or about 1-4, consecutive amino acids of the light chain.

TABLE 3

| Toxin | N-term (AAs 1-29) of LC | C-term (last 50 AAs) of LC | SEQ ID NO: |
|---|---|---|---|
| BoNT/A | PFVNKQFNYKDPVNGVDIAYIKI PNAGQM | GFNLRNTNLAANFNGQNTEINNM NFTKLKNFTGLFEFYKLLCVRGI ITSK | 47/48 |
| BoNT/B | PVTINNFNYNDPIDNDNIIMMEP PFARGT | YTIEEGFNISDKNMGKEYRGQNK AINKQAYEEISKEHLAVYKIQMC KSVK | 49/50 |
| BoNT/C1 | PITINNFNYSDPVDNKNILYLDT HLNTLA | NIPKSNLNVLFMGQNLSRNPALR KVNPENMLYLFTKFCHKAIDGRS LYNK | 51/52 |
| BoNT/D | TWPVKDFNYSDPVNDNDILYLRI PQNKLI | YTIRDGFNLTNKGFNIENSGQNI ERNPALQKLSSESVVDLFTKVCL RLTK | 53/54 |
| BoNT/E | PKINSFNYNDPVNDRTILYIKPG GCQEFY | GYNINNLKVNFRGQNANLNPRII TPITGRGLVKKIIRFCKNIVSVK GIRK | 55/56 |
| BoNT/F | PVAINSFNYNDPVNDDTILYMQI PYEEKS | TVSEGFNIGNLAVNNRGQSIKLN PKIIDSIPDKGLVEKIVKFCKSV IPRK | 57/58 |
| BoNT/G | PVNIKXFNYNDPINNDDIIMMEP FNDPGP | QNEGFNIASKNLKTEFNGQNKAV NKEAYEEISLEHLVIYRIAMCKP VMYK | 59/60 |

In some embodiments, the modified botulinum toxin comprises a tyrosine phosphorylation site, e.g., a tyrosine-based motif, that is located at the far most N-terminal region of the light chain of the toxin. For example, a modified botulinum toxin type A may comprise a light chain with an N-terminus starting as YKLLPFVNKQFNY . . . (wherein YKLL is the tyrosine-based motif). In some embodiments, the modified botulinum toxin comprises a tyrosine phosphorylation site, e.g., tyrosine-based motif, that is located within the first 1 to 10 amino acid residues of the N-terminal region of the light chain. In some embodiments, the modified botulinum toxin comprises a tyrosine-based motif that is located within the first 5 to 15 amino acid residues of the N-terminal region of the light chain. In some embodiments, the modified botulinum toxin comprises a tyrosine-based motif that is located within the first 10 to 20 amino acid residues of the N-terminal region of the light chain. In some embodiments, the modified botulinum toxin comprises a tyrosine-based motif that is located within the first 15 to 29 amino acid residues of the N-terminal region of the light chain.

In some embodiments, the modified botulinum toxin comprises a tyrosine phosphorylation site, e.g., a tyrosine-based motif, that is located at the far most C-terminal region of the light chain of the toxin. For example, a modified botulinum toxin type A may comprise a light chain with a C-terminus starting with . . . YKLLCVRGIITSKYKLL (wherein YKLL is the tyrosine-based motif). In some embodiments, the modified botulinum toxin comprises a tyrosine phosphorylation site, e.g., tyrosine-based motif, that is located within the last 1 to 10 amino acid residues of the C-terminal region of the light chain. In some embodiments, the modified botulinum toxin comprises a tyrosine-based motif that is located within the last 5 to 15 amino acid residues of the C-terminal region of the light chain. In some embodiments, the modified botulinum toxin comprises a tyrosine-based motif that is located within the last 10 to 20 amino acid residues of the C-terminal region of the light chain. In some embodiments, the modified botulinum toxin comprises a tyrosine-based motif that is located within the last 15 to 25 amino acid residues of the C-terminal region of the light chain. In some embodiments, the modified botulinum toxin comprises a tyrosine-based motif that is located within the last 20 to 30 amino acid residues of the C-terminal region of the light chain. In some embodiments, the modified botulinum toxin comprises a tyrosine-based motif that is located within the last 25 to 35 amino acid residues of the C-terminal region of the light chain. In some embodiments, the modified botulinum toxin comprises a tyrosine-based motif that is located within the last 30 to 40 amino acid residues of the C-terminal region of the light chain. In some embodiments, the modified botulinum toxin comprises a tyrosine-based motif that is located within the last 35 to 50 amino acid residues of the C-terminal region of the light chain.

In some embodiments, the modified botulinum toxin comprises a modified light chain and a heavy chain of the same type of botulinum toxin. In some embodiments, the modified botulinum toxin is a chimera comprising a modified light chain of one botulinum toxin type, and a heavy chain of another botulinum toxin type. The heavy chain may further be modified.

Although the present invention has been described in detail with regard to certain preferred methods, other embodiments, versions, and modifications within the scope of the present invention are possible. For example, a wide variety of modified neurotoxins can be effectively used in the methods of the present invention in place of *Clostridial* neurotoxins. Also, the corresponding genetic codes, i.e. DNA sequence, to the modified neurotoxins are also considered to be part of this invention. Additionally, the present invention includes peripheral administration methods wherein two or more modified neurotoxins, for example BoNT/E fused with a modification site and BoNT/B fused with a modification site, are administered concurrently or consecutively. Furthermore, a "targeting component" may be added to or substituted onto a modified neurotoxin of this invention. The "targeting component" may be a small molecule or a polypeptide having selective binding to a particular receptor. As such, a modified neurotoxin of the present invention comprising a targeting component may be specifically directed to a specific target receptor. See Foster et al in U.S. Pat. No. 5,989,545 and Donovan in U.S. patent application Ser. No. 09/489,667, the disclosures of which are incorporated herein by reference.

While this invention has been described with respect to various specific examples and embodiments, it is to be understood that the invention is not limited thereto and that it can be variously practiced with the scope of the following claims.

What is claimed is:

1. A botulinum neurotoxin type A comprising an amino acid modification at an N-glycosylation site, wherein botulinum neurotoxin type A can interfere with the functions of a neuron, and wherein the amino acid modification decreases biological persistence of the botulinum neurotoxin relative to a naturally-occurring botulinum neurotoxin type A without the amino acid modification.

2. The botulinum toxin type A of claim 1, wherein the amino acid modification is a deletion of at least one amino acid from the N-glycosylation site.

3. The botulinum toxin type A of claim 1, wherein the amino acid modification is a substitution of at least one amino acid from the N-glycosylation site.

4. The modified botulinum toxin type A of claim 1, wherein the N-glycosylation site is selected from the group consisting of SEQ ID NO: 1, SEQ ID NO: 2, SEQ ID NO: 3, SEQ ID NO: 4 and any combination thereof.

5. The botulinum toxin type A of claim 1, wherein the N-glycosylation site is SEQ ID NO: 1.

6. A botulinum neurotoxin type A comprising a botulinum neurotoxin comprising a proteolytic domain from the light chain of a clostridial neurotoxin and an amino acid modification of a N-glycosylation site, wherein the amino acid modification decreases biological persistence of the botulinum neurotoxin relative to a naturally-occurring botulinum neurotoxin type A without the amino acid modification.

7. The botulinum neurotoxin type A of claim 6, wherein the botulinum neurotoxin further comprises a $H_N$ fragment from the heavy chain of a Clostridial neurotoxin.

8. The botulinum neurotoxin type A of claim 6, wherein the botulinum neurotoxin further comprises a $H_C$ fragment derived from the heavy chain of a *Clostridial* neurotoxin.

9. The botulinum neurotoxin type A of claim 6, wherein the botulinum neurotoxin further comprises a $H_N$ fragment from the heavy chain of a *Clostridial* neurotoxin and a $H_C$ fragment derived from the heavy chain of a *Clostridial* neurotoxin.

10. The botulinum toxin type A of claim 6, wherein the amino acid modification is a deletion of at least one amino acid from the N-glycosylation site.

11. The botulinum toxin type A of claim 6, wherein the amino acid modification is a substitution of at least one amino acid from the N-glycosylation site.

12. The modified botulinum toxin type A of claim 6, wherein the N-glycosylation site is selected from the group consisting of SEQ ID NO: 1, SEQ ID NO: 2, SEQ ID NO: 3, SEQ ID NO: 4 and any combination thereof.

13. The botulinum toxin type A of claim 6, wherein the N-glycosylation site is SEQ ID NO: 1.

\* \* \* \* \*

UNITED STATES PATENT AND TRADEMARK OFFICE
CERTIFICATE OF CORRECTION

| | |
|---|---|
| PATENT NO. | : 7,893,202 B1 |
| APPLICATION NO. | : 11/624111 |
| DATED | : February 22, 2011 |
| INVENTOR(S) | : Lance E. Steward et al. |

Page 1 of 2

It is certified that error appears in the above-identified patent and that said Letters Patent is hereby corrected as shown below:

On the Title page, Item (56), under "OTHER PUBLICATIONS", line 23, delete "PoisoningCan." and insert -- Poisoning, Can. --, therefor.

On the Title page, Item (56), under "OTHER PUBLICATIONS", line 26, delete "Dichrosim" and insert -- Dichroism --, therefor.

In column 1, line 9, delete "each" and insert -- each of --, therefor.

In column 1, line 33, delete "parotoid" and insert -- parotid --, therefor.

In column 1, line 60, delete "Pharmcol." and insert -- Pharmacol. --, therefor.

In column 2, line 18, delete "Naunyn-schmiedeber's" and insert -- Naunyn-schmiedeberg's --, therefor.

In column 2, line 25, delete "Varshaysky A." and insert -- Varshavsky A. --, therefor.

In column 3, line 35-38, delete "This invention also provide for methods of producing modified neurotoxins. Additionally, this invention provide for methods of using the modified neurotoxins to treat biological disorders." and insert the same on Col. 3, Line 35 as a new paragraph.

In column 9, line 64, delete "Weigand" and insert -- Wiegand --, therefor.

Signed and Sealed this
Twentieth Day of December, 2011

David J. Kappos
*Director of the United States Patent and Trademark Office*

CERTIFICATE OF CORRECTION (continued)
U.S. Pat. No. 7,893,202 B1

In column 9, line 64, delete "Nauny-Schmiedeberg's" and insert -- Naunyn-Schmiedeberg's --, therefor.

In column 9, line 66, delete "Nauny-Schmiedeberg's " and insert -- Naunyn-Schmiedeberg's --, therefor.

In column 12, line 42, delete "orthoplasty meniscusectomy" and insert -- arthroplasty meniscectomy --, therefor.

In column 13, line 11, delete "catherization" and insert -- catheterization --, therefor.

In column 15, line 34, delete "a bout" and insert -- about --, therefor.